United States Patent [19]

Bohmholdt et al.

[11] 3,981,921
[45] Sept. 21, 1976

[54] PROCESS FOR PRODUCING KETONES

[75] Inventors: Gerd Bohmholdt, Westerholt;
Hinrich Husemann, Marl; Helmut Riedel, Gelsenkirchen-Buer, all of Germany

[73] Assignee: Veba-Chemie AG, Gelsenkirchen-Buer, Germany

[22] Filed: Dec. 21, 1970

[21] Appl. No.: 100,339

[30] Foreign Application Priority Data
Dec. 27, 1969 Germany............................ 1965186

[52] U.S. Cl................ 260/586 R; 260/596; 260/617 R; 260/631 R; 260/641
[51] Int. Cl.²...................................... C07C 45/00
[58] Field of Search.............. 260/641, 596, 586 R

[56] References Cited
UNITED STATES PATENTS

| | | | |
|---|---|---|---|
| 2,221,955 | 11/1940 | Schneider | 260/641 |
| 2,813,908 | 11/1957 | Young | 260/641 |
| 2,829,165 | 4/1958 | Coussemant | 260/596 |

*Primary Examiner*—James O. Thomas, Jr.
*Assistant Examiner*—A. Siegel
*Attorney, Agent, or Firm*—Burgess, Dinklage & Sprung

[57] ABSTRACT

In the process of making ketones by oxidizing olefins wherein olefins are first hydrated to secondary alcohols which are then dehydrogenated to ketones, the hydration step is carried out simultaneously with a liquid organic extraction step during which the secondary alcohols and ether by-product formed are absorbed and, following separation of the olefin-water phase, the secondary alcohols in the organic extracted phase are dehydrogenated and the ether by-product is purged.

9 Claims, 1 Drawing Figure

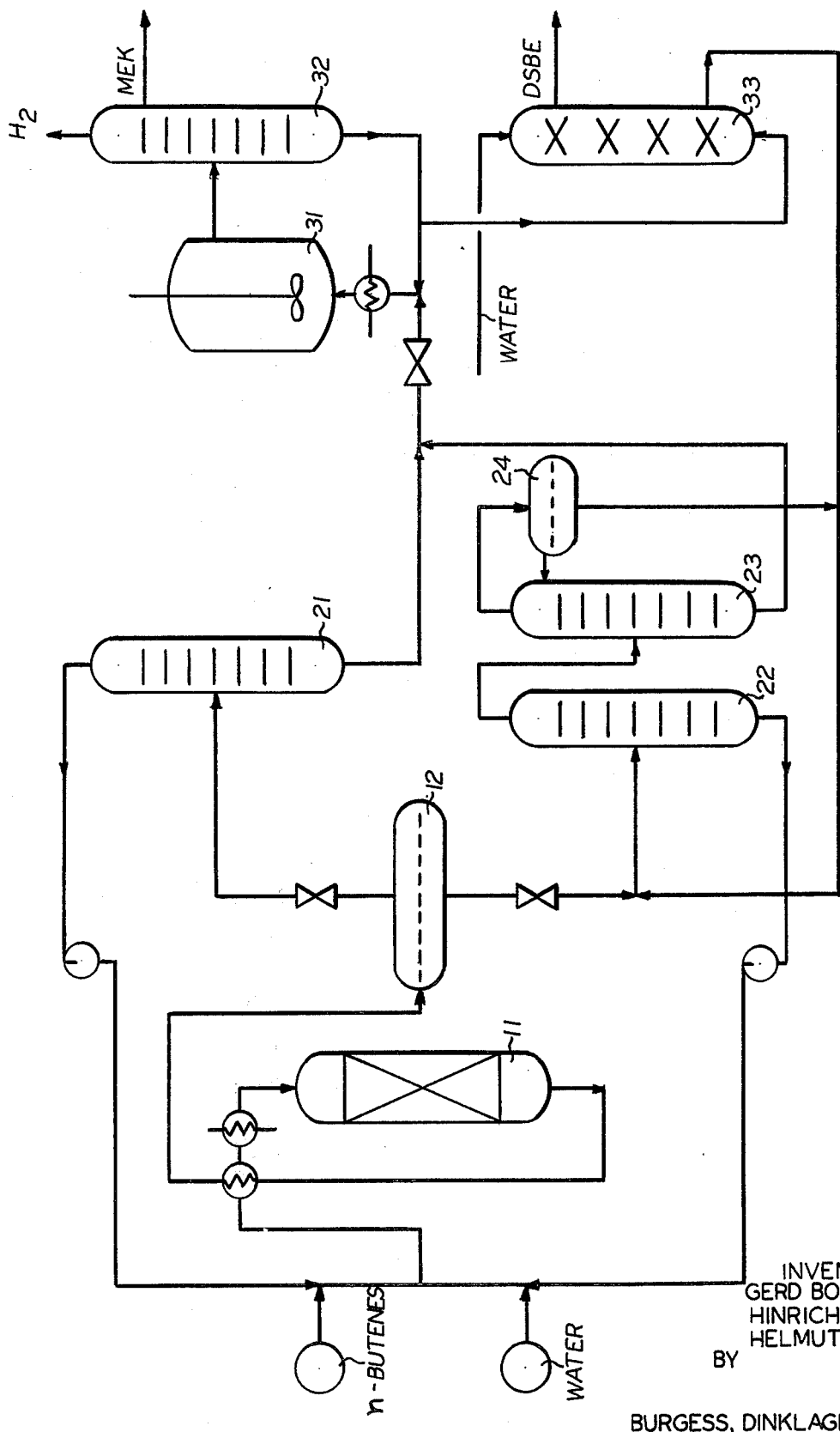

PROCESS FOR PRODUCING KETONES

BACKGROUND

The invention relates to a process for oxidizing olefins to ketones by first hydrating an olefin to form a secondary alcohol and then dehydrogenating the secondary alcohol to the corresponding ketone.

Methods of producing ketones have become known which begin with the direct oxidation of an olefin with oxygen or air, the ketone being classed, as a rule, only as a coupling product or by-product of an olefin oxide. An example of this method is the preparation of propene oxide and acetone from propene and oxygen in which isopropanol acts as the oxygen transfer agent.

Other known processes for oxidizing olefins to ketone use for the oxygen transfer the exchange of the charges of cations in aqueous solution, without the formation of the epoxide of the olefin. These processes have the common disadvantage of a low transformation combined with a low yield of ketones, plus a considerable tendency towards corrosion of the equipment.

In the processes known for the preparation of ketones through the production of secondary alcohols from olefins followed by dehydrogenation of the secondary alcohols to ketones, extraction of the secondary alcohol for the dehydrogenation step is performed in an aqueous phase only. For example, in the processes performed with catalysts in the gaseous phase, the secondary alcohol is washed out of the vapor phase with water. In this process olefins are absorbed in dilute sulfuric acid with the formation of esters which have to be cleaved hydrolytically with water to form alcohols and more dilute sulfuric acid.

In the methods of the prior art for the direct hydration of olefins on fixedly disposed sulfonic acid type artificial resin exchangers, such as the commercially available Lewatit S 100(Farbenfabriken BAyer AG) and Dowex 50W (Rohms & Haas Co.,) which permit the achievement of satisfactory yields even at medium temperatures, an aqueous phase is likewise utilized to extract the secondary alcohols.

SUMMARY

According to the present invention, hydration is accompanied by a simultaneous liquid organic phase extraction through a fixedly disposed catalyst bed in such a manner that a substantial portion of the secondary alcohols formed are absorbed into the liquid organic phase together with ether as the sole by-product and, after the separation of the olefin and water, all of the alcohol is delivered to a liquid-phase dehydrogenation system from which the ether accumulating in the alcohol is purged as for example through a lock.

THE DRAWING

The accompanying drawing is a flow diagram illustrating a preferred process of the present invention.

DESCRIPTION

Removing the secondary alcohols from the organic phase for the dehydrogenation step is simpler and easier than removing them from the aqueous phase. The ether, which is inert to the dehydrogenation reaction, is introduced together with the secondary alcohol into the dehydrogenation step where it accumulates and where it is more advantageous to remove it by purging, for example, than it is to remove it in the hydration stage as previously described.

The hydration of the olefins to secondary alcohols is performed at yields formations ranging from 2 to 20 mole-percent, preferably between 4 and 12 mole-percent and with selectiveness of better than 95 percent, ether occurring as the sole by-product. The hydration conditions are: temperatures between 80° and 160°C, pressures between 10 and 100 atmospheres absolute, water-to-olefin molar ratios between 0.1 and 10, and inputs of from 0.2 to 3 grams of olefin per gram of catalyst per hour.

The secondary alcohols are introduced into the dehydrogenation stage with ether contents between 2 and 50 weight-percent, and are there dehydrogenated to ketones with yields between 15 and 40 mole-percent and selectiveness of better than 95 percent, the ether accumulating in the circuit being removed by purging a quantity of circulating material corresponding to the amount of ether formed in the hydration stage, followed by washing with water, for example. The dehydrogenation of the secondary alcohols to ketones is preferably performed on a Raney nickel catalyst suspended in an inert reaction medium, e.g., high-boiling aliphatic hydrocarbons, at temperatures between 130° and 180°C and inputs between 1 and 4 grams of secondary alcohol per gram of catalyst per hour at atmospheric pressure.

For the purpose of achieving good retention time and distribution for the co-currently performed hydration and liquid phase extraction, the dispersion of the aqueous phase in the organic phase is performed and sustained, according to a preferred embodiment of the invention by means of hydrophilic packing bodies which are, at the same time, a catalyst for the hydration stage.

The following is an example of a preferred embodiment (with reference to the drawing) of the process of the invention for the production of methyl ethyl ketone from n-butenes.

The inputs of butene or butene-butane mixtures and fully desalted water are delivered together with the aqueous and organic returns through a cross-current heat exchanger and a peak preheater into the hydration reactor 11 through whose catalyst bed, composed of acid organic ion exchangers, they flow in the form of an aqueous/organic dispersion of liquid in liquid. The final reaction mixture, which contains, in addition to the unreacted starting substances, secondary butyl alcohol (SBA) as the main product and di-sec.-butyl ether (DSBE) as the sole by-product, is separated in separator 12 into an organic and an aqueous phase.

The organic phase, which absorbs most of the SBA and all of the DSBE, is dissociated in the distillation column 21 into butene or butene-butane mixture as the head product and SBA along with DSBE as the sump product.

The butene or the butene-butane mixture is recycled directly or through a processing stage to reactor 11. The aqueous phase is separated in distillation column 22 into the SBA-water azeotrope as the head product and water as the sump product, and the latter is recycled to the input to reactor 11. The azeotrope is subjected to an azeotropic distillation in the following column 23 with a suitable additive as the withdrawing agent, anhydrous SBA being produced in the sump. The thin SBA spirits drawn off at the phase separator 24 are recycled to 22.

The sump products flowing from columns 21 and 23 are combined and fed, together with most of the sump runoff from the distillation column 32, into the dehydrogenation reactor 31 where the reaction takes place on a Raney nickel catalyst suspended in an inert solvent, (a high-boiling paraffinic hydrocarbon).

The methyl ethyl ketone (MEK) that is formed is withdrawn from the final reaction mixture in the distillation column 32 at the side tap, and the hydrogen is removed at the head; the unreacted SBA together with the DSBE, which is inert in the dehydrogenation reactor, is withdrawn from the sump. Most of the sump runoff flows, as previously stated, back into the reactor 31. The rest is let off through a lock so as to keep the DSBE level constant, and is led into the extractor 33 where a highly concentrated DSBE is produced as a refinate and dilute SBA spirits are produced as an extract in a liquid-from-liquid extraction process using water. The dilute SBA spirits are recycled to column 22.

Representative experimental findings obtained in the hydration of n-butenes to sec. butanol and the dehydrogenation of sec. butanol to methyl ethyl ketone are set forth herewith.

TABLE 1

Experimental findings: hydration.
Catalyst: Lewatit S-100 cation exchanger in $H^+$ form.

| Experiment | No. 1 | No. 2 |
|---|---|---|
| Temperature (°C) | 130 | 140 |
| Pressure (atm. abs.) | 40 | 40 |
| Molar ratio (moles water:moles butene) | 5 | 3 |
| Input rate (g butenes: g catalyst/h) | 0.75 | 0.37 |
| Yield $\left(\frac{\text{moles sec. butanol}}{\text{moles butene in input}} \times 100\right)$ | 4.1 | 10.7 |
| Selectivity $\left(\frac{\text{moles sec. butanol}}{\text{moles butene reacted}} \times 100\right)$ | 99 | 95.8 |
| Distribution of yield $\left(\frac{\text{moles sec. butanol in org. phase}}{\text{moles sec. butanol in aqu. phase}}\right)$ | 3.4 | 4.8 |

TABLE 2

Experimental findings: dehydrogenation
Catalyst: Raney nickel

| Experiment | No. 1 | No. 2 |
|---|---|---|
| Temperature (°C) | 155 | 175 |
| Pressure (atm. abs.) | 1 | 1 |
| Input $\left(\frac{\text{g sec. butanol}}{\text{g cat.} \times h}\right)$ | 2 | 2 |
| Ether content of the input: $\left(\frac{\text{g sec. butyl ether}}{\text{g sec. butanol + g sec. butyl ether}} \times 100\right)$ | 15 | 40 |
| Yield $\left(\frac{\text{moles methyl ethyl ketone}}{\text{moles sec. butanol in input}} \times 100\right)$ | 18.4 | 27.4 |
| Selectivity $\left(\frac{\text{moles methyl ethyl ketone}}{\text{moles sec. butanol reacted}} \times 100\right)$ | 99 | 99 |

In a similar manner, higher straight-chained and branched as well as cyclic olefins can be converted into the corresponding ketones according to the process of the present invention. Generally, the olefin starting material contains from two to thirty carbons atoms and preferably from three to twenty carbon atoms.

Such olefins include for example ethylene, propylene, butene-1, butene-2, isobutylene, pentene-1, 2-methylbutene-1, 3-methylbutene-1, hexene-1, heptene-1, octene-1, cyclohexene, cyclooctene and the like.

In the present invention, as illustrated in the foregoing example, the starting olefin itself, either alone or in mixture with its corresponding alkane, is utilized as the extracting organic liquid for absorbing on the catalyst the secondary alcohols and ether formed during the hydration reaction. This is preferred since the need to later separate an independent extracting liquid is eliminated. For this purpose, it is only necessary to use an excess of starting olefin sufficient to effectively absorb the secondary alcohols and ether formed.

Of course, if desired, an added extracting fluid may be used and for this purpose any organic liquid which is inert under the conditions of the reaction and which selectively absorbs secondary alcohols and ethers over olefins and water may be employed. Such added organic liquid can later be separated by conventional separating techniques such as distillation and the like or it can be utilized as a medium for the dehydrogenation step and/or for the catalyst used in such step.

What is claimed is:

1. In a process for the oxidation of olefins to ketones by hydration at a temperature of 80° to 160°C and a pressure between 10 and 100 atmospheres followed by dehydrogenation at a temperature between 130° and 180°C of the secondary alcohols formed, the improvement which comprises carrying out simultaneously with the hydration an organic liquid phase extraction using the olefin starting material therefor on a fixedly disposed catalyst bed composed of acid organic ion exchangers thereby absorbing secondary alcohol and ether by-product formed, separating said liquid phase extract from the hydration reaction mixture, separating said secondary alcohol and ether from said liquid phase and thereafter feeding said secondary alcohol-ether mixture to a dehydrogenation step during which said ether is separated by purging.

2. Process of claim 1 wherein said catalyst bed is a sulfonic acid type resin exchanger.

3. Process of claim 1 wherein said olefin is mixed with its corresponding alkane.

4. Process of claim 1 wherein a substantial portion of secondary alcohol is absorbed by said extraction and the remaining portion thereof is recovered from the reaction mixture and combined with the secondary alcohol-ether mixture prior to dehydrogenation.

5. Process of claim 1 wherein the water to olefin molar ratio for said hydration is between 0.1 and 10, and the input of olefin is between 0.2 and 3 grams of olefin per gram of catalyst per hour.

6. Process of claim 1 wherein said dehydrogenation is carried out on a Raney nickel catalyst in an inert medium.

7. Process of claim 6 wherein said inert medium is a high boiling aliphatic hydrocarbon.

8. Process of claim 1 wherein the alcohol input is between 1 and 4 grams of secondary alcohol per gram of catalyst per hour.

9. Process of claim 1 wherein said hydration step is carried out in the presence of hydrophilic packing bodies as a catalyst and as a dispersion promoter.

* * * * *